United States Patent
Mizutani

(10) Patent No.: US 10,118,448 B2
(45) Date of Patent: Nov. 6, 2018

(54) TIRE INSPECTION APPARATUS FOR INSPECTING THE SIDEWALL OF THE TIRE

(71) Applicant: BRIDGESTONE CORPORATION, Tokyo (JP)

(72) Inventor: Akinobu Mizutani, Tokyo (JP)

(73) Assignee: BRIDGESTONE CORPORATION, Tokyo (JP)

(*) Notice: Subject to any disclaimer, the term of this patent is extended or adjusted under 35 U.S.C. 154(b) by 8 days.

(21) Appl. No.: 15/030,670

(22) PCT Filed: Oct. 16, 2014

(86) PCT No.: PCT/JP2014/077540
§ 371 (c)(1),
(2) Date: Apr. 20, 2016

(87) PCT Pub. No.: WO2015/064369
PCT Pub. Date: May 7, 2015

(65) Prior Publication Data
US 2016/0263952 A1  Sep. 15, 2016

(30) Foreign Application Priority Data
Nov. 1, 2013 (JP) .................................. 2013-228699

(51) Int. Cl.
*G01N 21/95* (2006.01)
*B60C 25/00* (2006.01)
(Continued)

(52) U.S. Cl.
CPC ........ *B60C 25/007* (2013.01); *B29D 30/0061* (2013.01); *B60C 19/00* (2013.01);
(Continued)

(58) Field of Classification Search
None
See application file for complete search history.

(56) References Cited

U.S. PATENT DOCUMENTS 6,124,925 A * 9/2000 Kaneko .............. B29D 30/0061
356/237.1
7,295,948 B2 * 11/2007 Jetter ................. B29D 30/0061
156/110.1
(Continued)

FOREIGN PATENT DOCUMENTS

CN    101163941 A    4/2008
CN    101896937 A    11/2010
(Continued)

OTHER PUBLICATIONS

Oct. 10, 2016 Extended Search Report issued in European Patent Application No. 14857345.4.
(Continued)

*Primary Examiner* — Peter Macchiarolo
*Assistant Examiner* — Jermaine Jenkins
(74) *Attorney, Agent, or Firm* — Oliff PLC

(57) ABSTRACT

In order to provide a tire inspection apparatus which is capable of identifying, when performing an appearance inspection of a tire, a location of a rubber burr from a captured image of a tire side and avoiding detection of the rubber burr as a defect in a subsequent inspection step using image processing, the tire inspection apparatus is provided with a storage unit for storing a model pattern of a molded object to be molded on the tire side to be inspected and a master image of the tire side, the master image being prepared when the molded object(s) and an unnecessary molded object(s) are molded together as a conforming article, a model pattern locating unit for locating the model pattern on the captured image of the tire side to be inspected in a position of the captured image showing a highest degree of agreement, and an unnecessary molded object location identifying unit for identifying a location of the unnecessary molded object from the captured image by comparing the
(Continued)

position of the model pattern located on the captured image against a position of the model pattern on the master image.

8 Claims, 3 Drawing Sheets

(51) Int. Cl.
| | |
|---|---|
| *B60C 19/00* | (2006.01) |
| *G01M 17/02* | (2006.01) |
| *G06K 9/62* | (2006.01) |
| *G06T 7/00* | (2017.01) |
| *B29D 30/00* | (2006.01) |
| *G01B 11/30* | (2006.01) |
| *G06T 7/33* | (2017.01) |
| *G06T 7/73* | (2017.01) |
| *G01B 11/25* | (2006.01) |
| *B29D 30/72* | (2006.01) |
| *B29K 21/00* | (2006.01) |
| *B29K 105/00* | (2006.01) |
| *B60C 13/00* | (2006.01) |

(52) U.S. Cl.
CPC ........... *G01B 11/30* (2013.01); *G01M 17/027* (2013.01); *G01N 21/95* (2013.01); *G06K 9/6203* (2013.01); *G06T 7/001* (2013.01); *G06T 7/337* (2017.01); *G06T 7/74* (2017.01); *B29D 30/72* (2013.01); *B29D 2030/0066* (2013.01); *B29K 2021/00* (2013.01); *B29K 2105/258* (2013.01); *B60C 13/001* (2013.01); *G01B 11/2522* (2013.01); *G06T 2207/10004* (2013.01); *G06T 2207/30108* (2013.01)

(56) References Cited

U.S. PATENT DOCUMENTS

| | | | | |
|---|---|---|---|---|
| 7,512,260 | B2* | 3/2009 | Murakami | G06T 7/0008 382/145 |
| 8,305,436 | B2* | 11/2012 | Fujisawa | G01M 17/027 348/92 |
| 8,498,467 | B2* | 7/2013 | Joly | G06T 7/33 382/141 |
| 8,948,491 | B2* | 2/2015 | Sekiguchi | G01B 11/30 356/600 |
| 9,097,514 | B2* | 8/2015 | Takahashi | G01B 11/0608 |
| 9,113,046 | B2* | 8/2015 | Fujii | G01B 11/25 |
| 9,123,112 | B2* | 9/2015 | Vinciguerra | G06K 9/6204 |
| 9,291,527 | B2* | 3/2016 | Zoken | G01M 17/027 |
| 9,310,278 | B2* | 4/2016 | Sukegawa | G01B 11/24 |
| 9,677,879 | B2* | 6/2017 | Mizutani | G01B 11/2522 |
| 2005/0058333 | A1* | 3/2005 | Kaneko | G01B 11/24 382/141 |
| 2007/0209431 | A1* | 9/2007 | Fujisawa | G01B 11/25 73/146 |
| 2009/0226073 | A1 | 9/2009 | Honda et al. | |
| 2011/0019903 | A1 | 1/2011 | Joly et al. | |
| 2013/0266189 | A1 | 10/2013 | Vinciguerra et al. | |
| 2016/0086320 | A1* | 3/2016 | Fujisawa | G06T 7/001 382/141 |
| 2016/0320265 | A1* | 11/2016 | Regoli | G01M 17/027 |

FOREIGN PATENT DOCUMENTS

| | | |
|---|---|---|
| CN | 102460132 A | 5/2012 |
| CN | 103210417 A | 7/2013 |
| EP | 1 750 089 A1 | 2/2007 |
| EP | 2500686 A1 | 9/2012 |
| JP | 2005-331274 A | 12/2005 |
| JP | 2007-011462 A | 1/2007 |
| JP | 2011-127930 A | 6/2011 |
| JP | 2011-226971 A | 11/2011 |
| JP | 2011-247646 A | 12/2011 |
| JP | 2013-096972 A | 5/2013 |
| WO | 2009/077539 A2 | 6/2009 |
| WO | 2012/055752 A1 | 5/2012 |

OTHER PUBLICATIONS

May 12, 2016 Written Opinion issued in International Patent Application No. PCT/JP2014/077540.

Dec. 16, 2014 Search Report issued in International Patent Application No. PCT/JP2014/077540.

Oct. 23, 2017 Search Report issued in Chinese Patent Application No. 201480060295.

* cited by examiner

FIG. 1
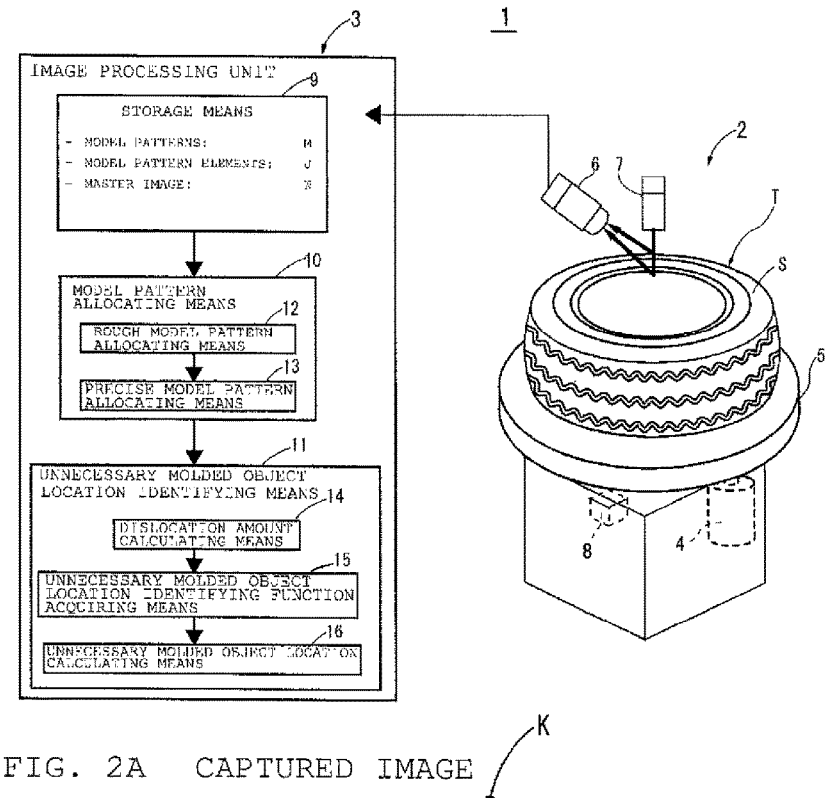
FIG. 2A   CAPTURED IMAGE
FIG. 2B   MASTER IMAGE
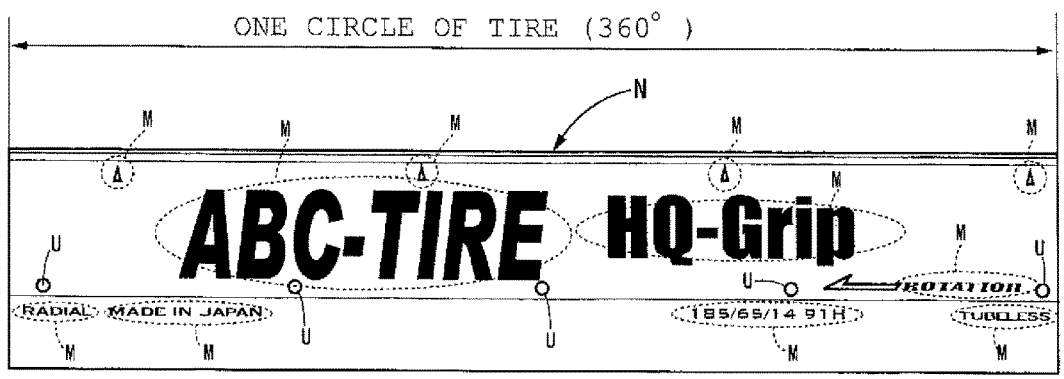

FIG. 3A
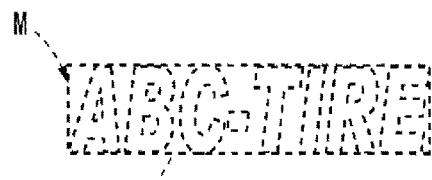
FIG. 3B
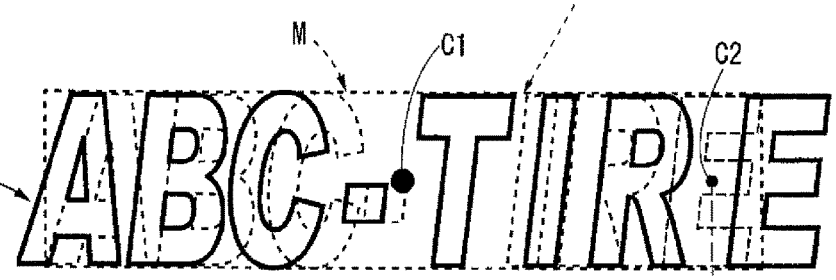
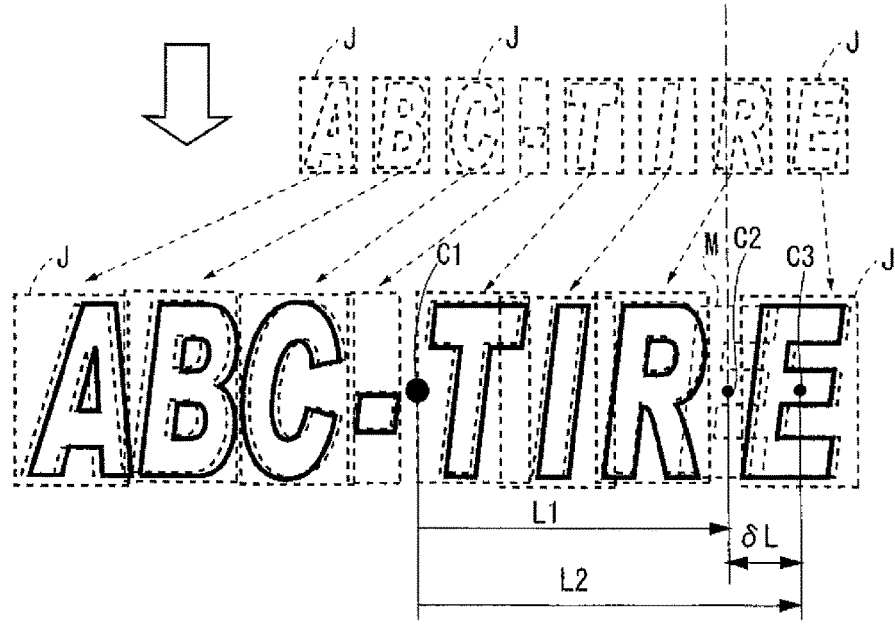

TIRE INSPECTION APPARATUS FOR INSPECTING THE SIDEWALL OF THE TIRE

TECHNICAL FIELD

The present invention relates to a tire inspection apparatus and more particularly to a tire inspection apparatus for inspecting molding defects by applying image processing to an image captured of a tire side along the circumferential direction of a tire.

BACKGROUND ART

In a conventional tire appearance inspection, a tire is placed on its side on a rotating table, and as the tire is rotated, an image of the upward tire side is captured along the circumferential direction of the tire. By doing so, an inspection image for one round of the tire side is obtained, and this inspection image is subjected to an image processing. Thus, an inspection is performed to detect molding defects, such as bumpy or recessed flaws, on the tire side (see Patent Document 1).

However, the tire side to be inspected has adhesions of rubber burrs which are rubber extremities having spilled into air bleeder holes provided in a mold for molding the tire or having spilled into gaps between the molds, in addition to the molded objects to be primarily molded. As a result, the inspection image obtained shows rubber burrs captured therein. And the rubber burrs captured in the inspection image are detected as defects because they cannot be distinguished from molding defects in an appearance inspection by image processing. Hence, parts detected as defects must be reinspected visually by a worker to determine whether they are molding defects or rubber burrs. This requires use of trouble and time for inspection, thus obstructing the improvement of efficiency in inspection.

RELATED ART DOCUMENT

Patent Document

Patent Document 1: Japanese Unexamined Patent Application Publication No. 2011-247646

SUMMARY OF THE INVENTION

Problems to be Solved by the Invention

Therefore, the object of the present invention is to provide a tire inspection apparatus that can improve the efficiency of inspection by eliminating the need for trouble and time for reinspection by a worker. This is done by identifying locations of rubber burrs in an image captured of a tire side in a tire appearance inspection and enabling an inspection of the tire side without detecting the rubber burrs as defects in a subsequent inspection step.

Means for Solving the Problem

A tire inspection apparatus to solve the above-described problem includes a storage means for storing a model pattern of a molded objects to be molded on a tire side of a tire to be inspected and a master image of the tire side, the master image being prepared when the molded object and an unnecessary molded object are molded together as a conforming article, a model pattern locating means for locating the model pattern on a captured image of the tire side to be inspected in a position of the captured image showing a highest degree of agreement with the model pattern, and an unnecessary molded object location identifying means for identifying a location of the unnecessary molded object from the captured image by comparing the position of the model pattern located on the captured image against a position of the model pattern on the master image.

This makes it possible to identify the locations of the unnecessary molded objects in the captured image. And it becomes possible to perform a tire side inspection without erroneously detecting the unnecessary molded object as a defect in a subsequent inspection step. As a result, the inspection efficiency can be improved by eliminating the need for trouble and time for reinspection by a worker.

BRIEF DESCRIPTION OF THE DRAWINGS

FIG. 1 is an overall schematic illustration of an inspection apparatus according to the present invention.

FIGS. 2A and 2B are illustrations showing an inspection image and a master image.

FIGS. 3A and 3B are diagrams showing a pattern matching by a model pattern locating means.

BEST MODE FOR CARRYING OUT THE INVENTION

Figure 4:
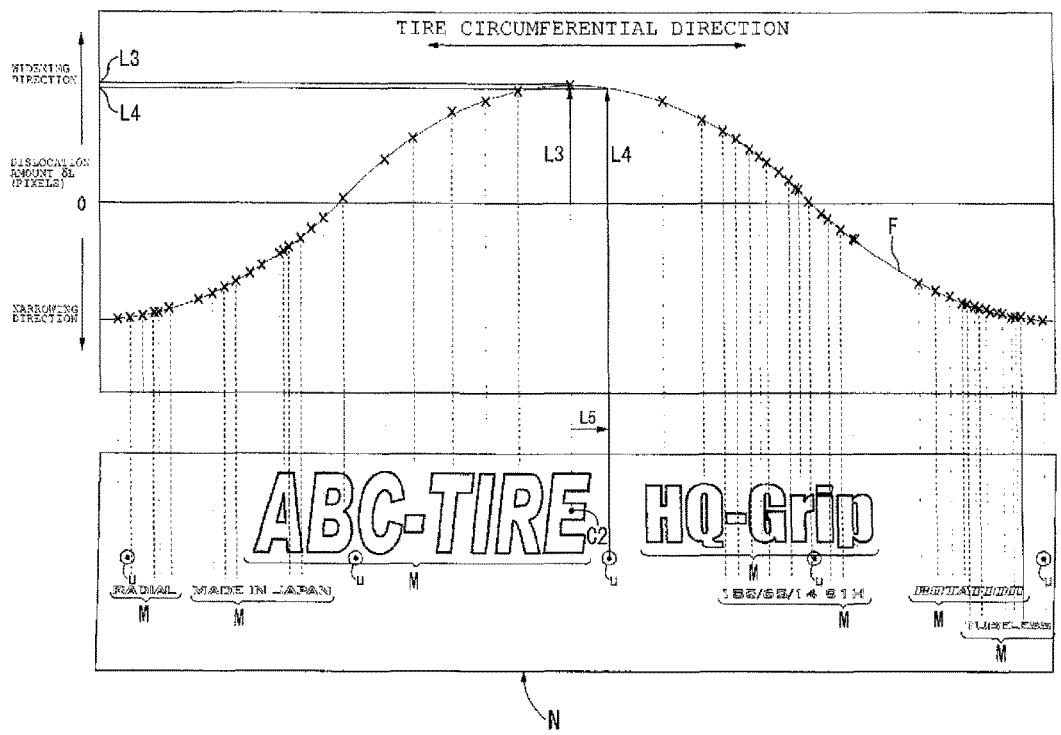
FIG. 4 is a diagram showing a relationship between dislocation amounts and a location identifying function in captured locations.

FIG. 1 is a schematic constitution diagram of an inspection apparatus 1 for a tire T implementing an embodiment of the present invention. FIG. 2A shows a captured image K captured by an image acquiring unit 2 shown in FIG. 1. FIG. 2B is a diagram showing a master image N stored beforehand by an image processing unit 3 shown in FIG. 1.

Hereinafter, a description is given of the inspection apparatus 1 for the tire T with reference to FIG. 1 and FIGS. 2A and 2B.

The inspection apparatus 1 according to the present invention makes it possible to perform an appearance inspection of a tire side S of the tire T by identifying a location of an unnecessary molded object from an image captured of the tire side S and enabling the appearance inspection without detecting the unnecessary molded object as a defect in a subsequent inspection step using image processing. And the inspection apparatus 1 includes an image acquiring unit 2 for capturing an image of the tire side S of the tire T to be inspected and an image processing unit 3.

With the tire T to be inspected without an internal pressure applied therein and placed on its side on a table 5 freely rotatable by a rotating mechanism 4, the image acquiring unit 2 captures an image of the state of the tire side S using a camera 6 and a light source 7 disposed above the table 5. The image is produced by casting a slit-shaped 2-dimensional laser light (slit light) on the tire side S from the light source 7 in such a manner that the light extends in the radial direction of the tire and capturing by the camera 6 the trace of the laser light cast on the tire side S. Thus, color tones on the surface of the tire side are acquired as brightness values, and raised and recessed portions as height information. This image is captured while the tire T is rotated such that a captured image K of one round of the tire continuously along the circumferential direction of the tire T is acquired. That is, the image acquiring unit 2 in this embodiment acquires the captured image K of the tire side S by a so-called light-section method. Each pixel constituting the captured image K contains the height information representing the raised and recessed portions on the tire side S and the brightness information. It is to be noted that one round of tire T rotation is detected by an encoder 8.

The captured image K captured by the camera 6 is processed with images of individual shots arranged in a series by the image processing unit 3 to be discussed in the following, as shown in FIG. 2A.

The image processing unit 3, which is a so-called computer, is equipped with a CPU as calculating means, a ROM and a RAM as storage means, and an I/O interface as communication means. The storage means 9 stores a model pattern (s) M of a molded object(s) to be molded on the tire side S of the tire T to be inspected and a master image N of the tire side S, which is prepared when the molded object (s) and a rubber burr (s) U as an unnecessary molded object (s) molded unnecessarily on the tire side S are molded as a conforming article. Also, the image processing unit 3 is equipped with a model pattern locating means 10 for locating the model pattern(s) M in a position(s) with the highest degree of agreement with the model pattern(s) M on a captured image K captured of the tire side S to be inspected and an unnecessary molded object location identifying means 11 for identifying the location(s) of the rubber burr(s) U molded as an unnecessary molded object(s) from the captured image K by comparing the location(s) in the captured image K of the model pattern(s) M located thereon against the location (s) of the model pattern(s) M on the master image N. The above two means perform their respective processings according to the program stored in the storage means 9.

Molded objects, as shown in FIG. 2A, are the raised and recessed portions molded by the mold on the tire side S, which are, for example, a maker name, a tire name (nickname), a tire size, a manufacturing country name, a radial marking, a tubeless marking, a slip sign marking, a rotation marking, a not-shown factory code, a serial number, a mold number, an asymmetric pattern, etc. Also, the unnecessary molded objects are objects, such as rubber burrs U or spews adhering to the tire side S having spilled into air holes in the mold, which are molded unavoidably at the time of molding the tire. If an unnecessary molded object is located at an air hole provided in a mold for molding the tire, then it will be possible to identify with certainty the location of the rubber burr having spilled into the air hole, which is a necessary feature in the mold.

Recorded in the master image N are the molded objects, such as the maker name, the tire name (nickname), the tire size, the manufacturing country name, the radial marking, the tubeless marking, the slip sign marking, the rotation marking, together with the unnecessary molded objects, such as the rubber burrs U, in their respective locations of the tire side S when molded as a conforming article.

The character strings of the above-mentioned molded objects, such as the maker name, the tire name (nickname), the tire size, the manufacturing country name, the radial marking, the tubeless marking, the slip sign marking, the rotation marking, are recorded as model patterns M in the storage means 9 of the image processing unit 3. At the same time, the characters constituting the above-mentioned character strings are individually recorded as model pattern elements J in the storage means 9. The characters, which are scattered about covering almost the entire region of the tire side, make it possible to identify the locations of the unnecessary molded objects in the captured image with greater certainty and accuracy.

The above-mentioned model patterns M, model pattern elements J, and master image N, are prepared based on CAD data used at the designing of the mold. The molded objects molded as a conforming article are molded by the grooves carved in the mold. Therefore, use of the CAD data at the time of designing the mold makes it possible to obtain the model patterns M, model pattern elements J, and master image N with excellent accuracy.

Also, recorded in the master image N are the rubber burrs U to be molded as the unnecessary molded objects. The rubber burrs U are located at the air bleeder holes in the CAD data of the mold. Hence, the locations of the air holes contained in the CAD data are strung, for instance, to the model patterns M or model pattern elements J which are the closest thereto, and they are recorded as location identification data, etc. in the storage means 9.

FIG. 3A is a conceptual diagram showing a pattern matching by a rough model pattern locating means 12, and FIG. 3B is a conceptual diagram showing a pattern matching by a precise model pattern locating means 13. Note that the solid lines in the figures represent the captured image K, and the broken lines the master image N.

The model pattern locating means 10 is equipped with the rough model pattern locating means 12 and the precise model pattern locating means 13.

As shown in FIG. 3A, the rough model pattern locating means 12 performs pattern matching of a plurality of model patterns M to the captured image K and locates the model patterns M on the captured image K where the highest degree of agreement is shown respectively.

As shown in FIG. 3B, the precise model pattern locating means 13 performs pattern matching of model pattern elements J of the model patterns M matched by the rough model pattern locating means 12 in the vicinity of the locations matched by the rough model pattern locating means 12 and locates the model pattern elements J in locations of the highest degree of agreement. That is, at the precise model pattern locating means 13, pattern matching of model pattern elements J is executed within predetermined limits from the reference locations of the model patterns M matched on the captured image K, and the respective model pattern elements J are individually located on the captured image K. And the locations of the model pattern elements J located by the precise model pattern locating means 13 can be assumed to be the locations of the molded objects corresponding to the model pattern elements J matched to the captured image K.

Hereinbelow, a description is given of the operation of the model pattern locating means 10, using the model pattern of maker name "ABC-TIRE".

First, the model pattern "ABC-TIRE" is located over the captured image K by the rough model pattern locating means 12.

Next, with reference to the location of the model pattern "ABC-TIRE" matched to the captured image K, pattern matching is again executed using "A", "B", "C", "-", "T", "I", "R", "E" as the model pattern elements J constituting the model pattern "ABC-TIRE" relative to the "ABC-TIRE" on the captured image K by the precise model pattern locating means 13, thereby locating the model pattern elements J on the captured image K.

The unnecessary molded object location identifying means 11 is equipped with a dislocation amount calculating means 14 for identifying the location of unnecessary molded object from the captured image K by comparing the locations on the captured image K of the model patterns M and the model pattern elements J located thereon against the locations of the model patterns M on the master image N. And it is further equipped with an unnecessary molded object location identifying function acquiring means 15 and an unnecessary molded object location calculating means 16.

The dislocation amount calculating means 14 calculates the dislocation amounts δL between the locations of the model pattern elements J located on the captured image K, as the model patterns M, when the model patterns M are matched to the captured image K by the rough model pattern locating means 12 and the locations of individual model pattern elements J located on the captured image K when the model pattern elements J are matched to the captured image K by the precise model pattern locating means 13.

This process is hereby explained taking "E" of the model pattern elements J of "ABC-TIRE" as an example. As shown in FIG. 3B, the distance L1 from the center C1 of the model pattern M "ABC-TIRE" (in broken lines) located in the captured image K when the model pattern M is matched to the captured image K by the rough model pattern locating means 12 to the center C2 of the model pattern element "E" (in broken lines) of the model pattern M and the distance L2 from the center C1 of "ABC-TIRE" to the center C3 of the model pattern element "E" (in broken lines) when the model pattern elements J are matched to the captured image K by the precise model pattern locating means 13 are obtained. And then the difference (distance L2−distance L1) is calculated as the dislocation amount δL.

It is to be noted here that the centers C1, C2, and C3 are the gravity center positions used as matching centers in pattern matching.

And this calculation is performed for each of the remaining model pattern elements J, namely, "A", "B", "C", "-", "T", "I", and "R" which constitute the model pattern M matched to the captured image K. Thus calculated are the dislocation amounts δL between the characters which are the elements of the molded object "ABC-TIRE" on the captured image K and the "A", "B", "C", "-", "T", "I", "R", "E" of the model pattern elements J which are the elements of "ABC-TIRE" of the model pattern M on the master image N.

The above calculation of dislocation amount δL is done for all of the model pattern elements of all the model patterns M. All these calculated dislocation amounts δL are strung to the respective model pattern elements J at the time of calculation of the dislocation amounts δL and stored in the storage means 9.

As shown in FIG. 4, when the dislocation amount δL calculated by using the above formula is greater than the reference value 0, the dislocation between the elements of the molded object, namely, the interval between characters here, is wider because the image is captured farther from the center of the table 5. And when the dislocation amount δL is smaller than the reference value 0, the dislocation between the elements of the molded object, namely, the interval between characters here, is narrower because the image is captured closer to the center of the table 5.

It is to be noted that when the matching rate in the matching of each character is the threshold value or below, the matching rate is not used for the processing, and the dislocation amount δL of the particular character is ignored in the subsequent processing. Also, the length of the dislocation amount δL is in the units of pixels in the captured image K.

The unnecessary molded object location identifying function acquiring means 15 executes a processing to acquire a location identifying function F for identifying the locations of rubber burrs U in the captured image K using the dislocation amount δL of every character derived by the dislocation amount calculating means 14.

The location identifying function F is a function represented by dislocation amounts δL between the locations of the model pattern elements J contained in the master image N in the circumferential direction of the tire and the characters in the respective locations contained in the captured image K corresponding to the model pattern elements J.

More specifically, as shown in FIG. 4, a diagram is set with the horizontal axis representing the tire circumferential direction along the circumferential direction of the master image N and the vertical axis representing the dislocation amount δL. Then the dislocation amounts δL strung to the position of the center C2 on the master image N of the respective model pattern elements J calculated by the dislocation amount calculating means 14 are mapped on the diagram. And the location identifying function F is obtained as an approximate curve connecting the mapped points. As shown in FIG. 4, the shape of the location identifying function F as an approximate curve connecting the mapped points is substantially the same as a sine curve.

That is, the molded objects are scattered about covering almost the entire region in the circumferential direction of the tire side S. Therefore, by deriving the dislocation amounts δL along the circumferential direction at the respective locations of the model pattern elements J corresponding to the molded objects on the tire side S, it is possible to acquire the location identifying function F representing the state or tendency of dislocation of the molded objects or unnecessary molded objects at the various locations of the captured image K with excellent accuracy. And by use of this location identifying function F, it is possible to identify the locations of unnecessary molded objects from the captured image K with certainty and accuracy.

The unnecessary molded object location calculating means 16 executes a processing to identify the locations of rubber burrs U from the captured image K using the above-described location identifying function F.

As shown in FIG. 2B, the locations in the tire circumferential direction of the rubber burrs U together with the molded objects are recorded in the master image N. Therefore, the locations of rubber burrs U can be easily identified from the locations of the model patterns M or model pattern elements J in the master image N.

Figure 5A:
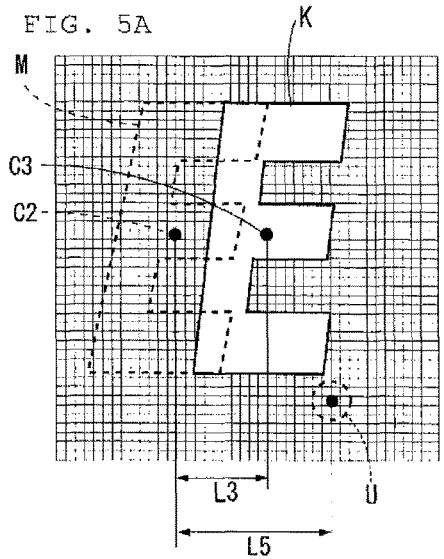
FIGS. 5A and 5B are diagrams showing a method for identifying the locations of rubber burrs in an inspection image.
Figure 5B:
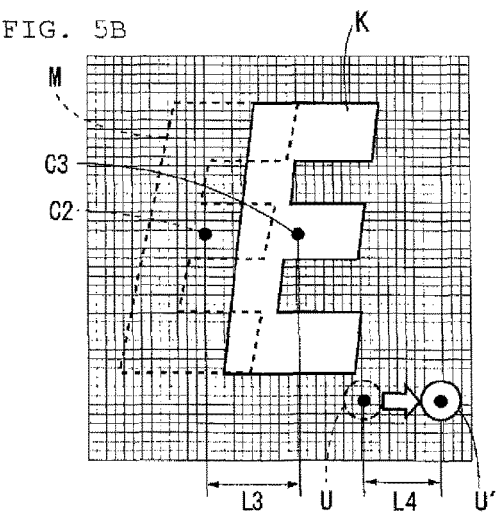

For example, let us assume a case where a rubber burr U is recorded at the location dislocated in the circumferential direction by a distance L5 from the center C2 of the model pattern element "E" in the master image N as shown in FIG. 5A. Then the value of dislocation amount δL of the location at the distance L5 in the circumferential direction from the location equal to the center C2 of the model pattern element "E" is calculated from the location identifying function F as shown in FIG. 4. In this manner, the location of actual rubber burr U' can be identified in the captured image K. That is, by referencing the location identifying function F, the location of the rubber burr U in the master image N is identified as the rubber burr U' at the location dislocated in the circumferential direction by the distance L4 from the center of the rubber burr U as shown in FIG. 5B.

This calculation of dislocation amount L4 is performed for all the rubber burrs U. Thus, the locations of all the rubber burrs U' captured in the captured image K can be identified with certainty and accuracy.

The identification in this manner of the locations of rubber burrs U' on the captured image K by the unnecessary molded object identifying means 11 can be processed easily by stringing and recording the relations between the rubber burrs U and the characters closest thereto in the storage means 9 beforehand. In other words, the distance L5 in the tire circumferential direction between the matching center C2 of the character "E" in the master image N and the matching center C4 of the rubber burr U is strung to the character "E" beforehand as shown in FIG. 5A. In doing so, the location of the rubber burr U' in the captured image K can be identified immediately when the function as shown in FIG. 4 is obtained.

Therefore, the positional relationships between the model pattern elements J constituting the character strings of the model patterns M of the character strings to be molded on the tire side S and the rubber burrs U in the master image N must be made known values in advance. Thus, it is possible to identify with ease and accuracy the locations of rubber burrs U' contained in the captured image K from the molded objects corresponding to the model pattern elements J.

The rubber burrs U' identified in the captured image K as described above are mask-processed by a processing means in a subsequent step such that they would not be detected as molding defects by an inspecting means because the height information contained in the captured image K is equalized to the height of the neighboring tire surfaces.

Hereinbelow, a description is given of the operation of the above-mentioned inspection apparatus 1.

First the image acquiring unit 2 acquires a captured image K by capturing images of the tire side S. This captured image K is captured as the table 5 is rotated with a tire T placed on its side on the table 5 without applying an internal pressure into the tire. As a result, the captured image K is obtained in a condition where the rotation center of the tire T and the rotation center of the table 5 are not in agreement with each other and the tire T itself is not taut because of its pliability. That is, the images constituting the captured image K are captured with different pixel widths in the circumferential direction. Consequently, as shown in FIG. 2A and FIG. 2B, the captured image K, in comparison with the master image N, may have parts where the characters are squeezed together to have the interval between them narrower and parts where the characters extend in the tire circumferential direction to have the interval therebetween wider.

Next, the locations of rubber burrs U', which are unnecessary molded objects, are identified from the captured image K by the image processing unit 3.

Firstly, the image processing unit 3 locates the model patterns M on the captured image K by performing pattern matching on the captured image K of the model patterns M, such as maker name, tire name (nickname), tire size, manufacturing country name, radial marking, tubeless marking, slip sign marking, and rotation marking, contained in the master image N as shown in FIG. 2B, using the rough model pattern locating means 12 of the model pattern locating means 10.

Next, by the precise model pattern locating means 13, the model pattern elements J of the model patterns M matched by the rough model pattern locating means 12 are located on the captured image K by pattern-matching them within predetermined limits on the captured image K with reference to the locations matched by the rough model pattern locating means 12.

Then, by the dislocation amount calculating means 14 of the unnecessary molded object location identifying means 11, calculation processing is executed of the dislocation amounts δL between the locations of the characters located on the captured image K captured for inspection and the corresponding locations of the characters on the master image N.

This calculation of dislocation amount δL is done for all the model pattern elements J constituting all the model patterns M.

Then, by the unnecessary molded object location identifying function acquiring means 15, the location identifying function F for identifying the locations of rubber burrs U from the dislocation amounts δL of the respective characters on the captured image K is obtained.

Then, by the unnecessary molded object location calculating means 16, the locations of the rubber burrs U' as unnecessary molded objects are identified using the location identifying function F. This identification of the locations of the rubber burrs U' is executed for all the rubber burrs U contained in the master image N. As a result, all the locations of the rubber burrs U' contained in the captured image K are identified with accuracy.

By implementing the structure as described above, it is possible to identify the locations of rubber burrs U' from the captured image K with certainty and accuracy even when the tire T is rotating eccentrically relative to the camera 6 or when the tire side S is not taut at the time of capturing an inspection image. This allows an inspection to be conducted without detecting the rubber burrs by such a process as ignoring the rubber burrs U' identified as described above in a subsequent inspection step using image processing. As a result, it is no longer necessary for the worker to perform a reinspection to distinguish visually between molding defects and rubber burrs. Accordingly, it becomes possible to shorten the time and improve inspection efficiency without trouble taken for inspection.

In the present embodiment, in particular, the captured image K is captured of the tire side S without the internal pressure applied to the tire. In such cases, the circumferential lengths of the captured image K vary with the capturing positions because of the eccentricity or deformation of the tire at the time of image capturing. Hence, the locations of rubber burrs U cannot be identified by directly comparing the captured image K against the CAD data at the time of mold design. However, according to the method of the present invention, it is advantageously possible to identify rubber burrs U' from the captured image K with certainty without being affected by the eccentricity or deformation at the time of image capturing.

As another structure of the inspection apparatus 1, it is possible to eliminate the precise model pattern locating means 13 in the above-described processing when the tire T to be inspected can be fitted to the rim and the internal pressure can be applied to the tire in the acquisition of the captured image K by the image acquiring unit 2. That is, with the tire T fitted to the rim and the internal pressure applied within the tire, there is almost no change in the distance of the tire side S relative to the camera 6 at the rotation of the tire (no effect of the deformation of the tire T and eccentricity at the time of image capturing). There will be the effects only of the differences from the CAD data due to the deformation of the tire side S when the internal pressure is applied. That is, there will be only isotropic changes of the locations of the model patterns M between themselves in the circumferential direction and the radial direction in the master image N. Therefore, the locations of the rubber burrs U may be identified from the captured image K by locating the model patterns M on the captured image K by pattern matching by the rough model pattern locating means 12 and obtaining the location identifying function F after calculating the dislocation amounts δL between the model patterns M and the captured image K by the dislocation amount calculating means 14.

DESCRIPTION OF REFERENCE NUMERALS 1 inspection apparatus
2 image acquiring unit
3 image processing unit
9 storage means
10 model pattern locating means
11 unnecessary molded object location identifying means
12 rough model pattern locating means
13 precise model pattern locating means
14 dislocation amount calculating means
15 unnecessary molded object location identifying function acquiring means
16 unnecessary molded object location calculating means
F location identifying function
K captured image
M model pattern
N master image
U rubber burrs

The invention claimed is:

1. A tire inspection apparatus configured to inspect a tire side of a tire to be inspected, the tire inspection apparatus comprising:
an image capture device configured to create a captured image of the tire side of the tire to be inspected;
a storage device configured to store:
(i) a model pattern of a molded object to be molded on the tire side of the tire to be inspected, and
(ii) a master image of the tire side, the master image being prepared when the molded object and an unnecessary molded object are molded together as a conforming article; and
a processor configured to perform the following:
locate the model pattern on the captured image of the tire side to be inspected in a position of the captured image showing a highest degree of agreement with the model pattern; and
identify a location of the unnecessary molded object from the captured image by comparing the position of the model pattern located on the captured image against a position of the model pattern on the master image.

2. The tire inspection apparatus according to claim 1, wherein the model pattern comprises characters constituting a character string to be molded on the tire side.

3. The tire inspection apparatus according to claim 2, wherein the processor is configured to calculate a dislocation amount of the position of the model pattern located on the captured image from the position of the model pattern on the master image, and add the dislocation amount to the location of the unnecessary molded object relative to the molding object in the master image and identifies the location of the unnecessary molded object on the captured image.

4. The tire inspection apparatus according to claim 3, wherein the unnecessary molded object is an air hole provided in a mold for molding the tire.

5. The tire inspection apparatus according to claim 2, wherein the unnecessary molded object is an air hole provided in a mold for molding the tire.

6. The tire inspection apparatus according to claim 1, wherein the processor is configured to calculate a dislocation amount of the position of the model pattern located on the captured image from the position of the model pattern on the master image, and add the dislocation amount to the location of the unnecessary molded object relative to the molding object in the master image and identifies the location of the unnecessary molded object on the captured image.

7. The tire inspection apparatus according to claim 6, wherein the unnecessary molded object is an air hole provided in a mold for molding the tire.

8. The tire inspection apparatus according to claim 1, wherein the unnecessary molded object is an air hole provided in a mold for molding the tire.

* * * * *